United States Patent
Scofield (10) Patent No.: US 9,685,078 B2
(45) Date of Patent: Jun. 20, 2017

(54) TRAFFIC FLOW RATES

(71) Applicant: INRIX INC., Kirkland, WA (US)

(72) Inventor: Christopher L. Scofield, Seattle, WA (US)

(73) Assignee: INRIX INC., Kirkland, WA (US)

( * ) Notice: Subject to any disclaimer, the term of this patent is extended or adjusted under 35 U.S.C. 154(b) by 0 days.

(21) Appl. No.: 15/123,244

(22) PCT Filed: Mar. 3, 2015

(86) PCT No.: PCT/US2015/018400
§ 371 (c)(1),
(2) Date: Sep. 1, 2016

(87) PCT Pub. No.: WO2015/134434
PCT Pub. Date: Sep. 11, 2015

(65) Prior Publication Data
US 2017/0076594 A1    Mar. 16, 2017

(51) Int. Cl.
*G08G 1/065* (2006.01)
*G08G 1/01* (2006.01)
*H04W 4/04* (2009.01)

(52) U.S. Cl.
CPC ......... *G08G 1/0112* (2013.01); *G08G 1/0129* (2013.01); *G08G 1/0141* (2013.01);
(Continued)

(58) Field of Classification Search
CPC .... G08G 1/0129; G08G 1/0145; G08G 1/065; H04W 4/046
See application file for complete search history.

(56) References Cited

U.S. PATENT DOCUMENTS

| 5,559,864 A | 9/1996 | Kennedy, Jr. |
| 6,708,085 B2 | 3/2004 | Yamane et al. |

(Continued)

FOREIGN PATENT DOCUMENTS

CN    102855759 A    2/2013

OTHER PUBLICATIONS

Corresponding International Application No. PCT/US15/18400, International Search report and written opinion dated Jun. 10, 2015.

*Primary Examiner* — Joseph Feild
*Assistant Examiner* — Rufus Point
(74) *Attorney, Agent, or Firm* — Cooper Legal Group, LLC (57) ABSTRACT

One or more techniques and/or systems are provided for determining a scaled flow rate of traffic for a road segment. For example, probe flow rate information is determined based upon locational information from one or more probe vehicles on a road segment (e.g., a flow rate of probe vehicles corresponding to a sum of probe vehicles identified from time stamped global positioning system coordinates provided by the probe vehicles). Satellite imagery of the road segment is analyzed to identify a count of vehicles on the road segment. Scale factor and offset information is estimated based upon the probe flow rate information and the count of vehicles. The scale factor and offset information is used to scale the probe flow rate information to determine a scaled flow rate that may be a relatively accurate flow rate of traffic, which may correspond to an inferred traffic volume along the road segment.

20 Claims, 7 Drawing Sheets

(52) U.S. Cl.
  CPC .......... *H04W 4/046* (2013.01); *G08G 1/0145* (2013.01); *G08G 1/065* (2013.01)

(56) References Cited

U.S. PATENT DOCUMENTS

| | | | | |
|---|---|---|---|---|
| 8,433,505 | B2* | 4/2013 | Rogers | G08G 1/0104 340/992 |
| 8,682,571 | B2* | 3/2014 | Chapman | G01C 21/3691 701/117 |
| 8,738,283 | B2* | 5/2014 | Zhou | G01C 21/3611 701/400 |
| 8,880,324 | B2* | 11/2014 | Chapman | G01C 21/3691 701/119 |
| 8,909,463 | B2* | 12/2014 | Chapman | G01C 21/3691 701/118 |
| 9,250,079 | B2* | 2/2016 | Zhou | G01C 21/3611 |
| 9,280,894 | B2* | 3/2016 | Chapman | |
| 9,518,833 | B2* | 12/2016 | Fink | G01C 21/3492 |
| 2006/0158330 | A1 | 7/2006 | Gueziec | |
| 2010/0151838 | A1* | 6/2010 | Wormald | G08G 1/096716 455/414.1 |
| 2010/0256863 | A1* | 10/2010 | Nielsen | G07C 5/085 701/31.4 |
| 2011/0043377 | A1 | 2/2011 | McGrath et al. | |
| 2011/0115648 | A1 | 5/2011 | Laurgeau et al. | |
| 2011/0160988 | A1* | 6/2011 | Rogers | G08G 1/0104 701/119 |
| 2011/0161001 | A1* | 6/2011 | Fink | G01C 21/3492 701/533 |
| 2011/0184640 | A1* | 7/2011 | Coleman | G01C 21/3492 701/533 |
| 2011/0231091 | A1* | 9/2011 | Gourlay | G08G 1/0104 701/465 |
| 2012/0078504 | A1* | 3/2012 | Zhou | G01C 21/3611 701/411 |
| 2013/0124075 | A1* | 5/2013 | Rothschild | G08G 1/017 701/119 |
| 2013/0195362 | A1 | 8/2013 | Janky et al. | |
| 2013/0197790 | A1* | 8/2013 | Ouali | G08G 1/0133 701/118 |
| 2014/0085112 | A1* | 3/2014 | Gruteser | B60Q 9/004 340/932.2 |
| 2014/0114562 | A1* | 4/2014 | Zhou | G01C 21/3611 701/410 |
| 2014/0365126 | A1* | 12/2014 | Vulcano | G01C 21/36 701/533 |
| 2015/0097975 | A1* | 4/2015 | Nash | H04N 5/217 348/208.1 |
| 2016/0232787 | A1* | 8/2016 | Wakayama | G08G 1/0116 |

* cited by examiner

TRAFFIC FLOW RATES

CROSS-REFERENCE TO RELATED APPLICATIONS

This application claims priority to U.S. Provisional Patent Application No. 61/946,962 titled "DETERMINING HOV/HOT LANE TRAVEL TIMES", filed on Mar. 3, 2014, which is hereby incorporated by reference.

BACKGROUND

Many users utilize various devices to obtain route information from a route provider. In an example, a user may utilize a smart phone to obtain driving directions to a nearby restaurant. In another example, a user may utilize a vehicle navigation device to obtain a map populated with driving directions to an amusement park. The route provider may be able to provide relatively more accurate and efficient routes to users if the route provider has information relating to traffic volumes, flow rates, congestion, accidents, traffic obstructions, etc. Traffic volume and flow rates may be identified from probe flow rate information derived from locational information, from probe vehicles, such as time stamped global positioning system (GPS) coordinates. Unfortunately, the probe flow rate information may merely represent a small portion of the actual vehicles on the road. For example, less than 2% of the vehicles may provide probe flow rate information for a road segment, and thus the probe flow rate information may need to be scaled to the total amount of traffic. However, the total amount of traffic may be unknown, and thus the scale factor may be imprecise. If relatively more accurate traffic volume and flow rate information could be identified, then city planning, measurement of business activity, the flow of demographic groups, travel route planning, and/or other information may be more accurately determined.

SUMMARY

This summary is provided to introduce a selection of concepts in a simplified form that are further described below in the detailed description. This summary is not intended to identify key factors or essential features of the claimed subject matter, nor is it intended to be used to limit the scope of the claimed subject matter.

Among other things, one or more systems and/or techniques for determining a scaled flow rate of traffic for a road segment are provided herein. Probe flow rate information may be determined based upon locational information from one or more probe vehicles on a road segment (e.g., a count of probe vehicles on the road segment). For example, the probe flow rate information may be derived from locational information, such as global positioning system (GPS) coordinates and timestamps, received from the one or more probe vehicles. Satellite imagery, such as an image or a video, of the road segment may be obtained. The satellite imagery may be analyzed to identify a count of vehicles on the road segment for a unit of time (e.g., linear features and/or a road network overlaid the satellite imagery may be used to identify the road segment, and parallelograms or other shape features may be used to identify vehicles).

Scale factor and offset information may be estimated based upon the probe flow rate information and the count of vehicles for the unit of time. The probe flow rate information may be scaled based upon the scale factor and offset information to determine a scaled flow rate (e.g., 3 probe vehicles may have provided locational information for the road segment and 30 vehicles may have been counted for the road segment, and thus the probe flow rate may be scaled by 10).

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

The claimed subject matter is now described with reference to the drawings, wherein like reference numerals are generally used to refer to like elements throughout. In the following description, for purposes of explanation, numerous specific details are set forth to provide an understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for determining a scaled flow rate of traffic for a road segment are provided herein. Traffic volume and flow rate information may be useful for city planning, measuring business activity, tracking the flow of demographic groups between locales, generating travel routes for users, and/or a variety of other uses. Unfortunately, determining a flow rate by scaling probe flow rate information, derived from locational information provided by probe vehicles, based upon an estimate of the percentage of traffic that such probe vehicles represent may be inaccurate because the percentage may be unknown and thus an estimated guess may be used (e.g., the number of probe vehicles providing locational information, such as global positioning system (GPS) coordinates, used to determine a probe flow rate may merely represent 2% or less of the actual traffic along a road segment). Road sensors may be used to obtain flow rates, however, road sensors may not be located along road segments of interest and may not provide lane counts or other relatively accurate information. Accordingly, as provided herein, satellite imagery may be used to identify a count of vehicles on a road segment. The count of vehicles and probe flow rate information may be used to estimate scale factor and offset information that may be used to scale probe flow rates to determine scaled flow rates. Scaled flow rates may be relatively more accurate indicators of traffic volumes and flow rates than merely scaling probe flow rates using estimated guesses of scaling factors because the scale flow rates are derived from relatively accurate counts of vehicles. In this way, relatively more accurate information of traffic volumes and flow rates may be used to provide more accurate and efficient travel routes, city planning, measurements of business activity, flow of demographic groups, and/or other use cases of traffic volume and flow rate information.

Figure 1:
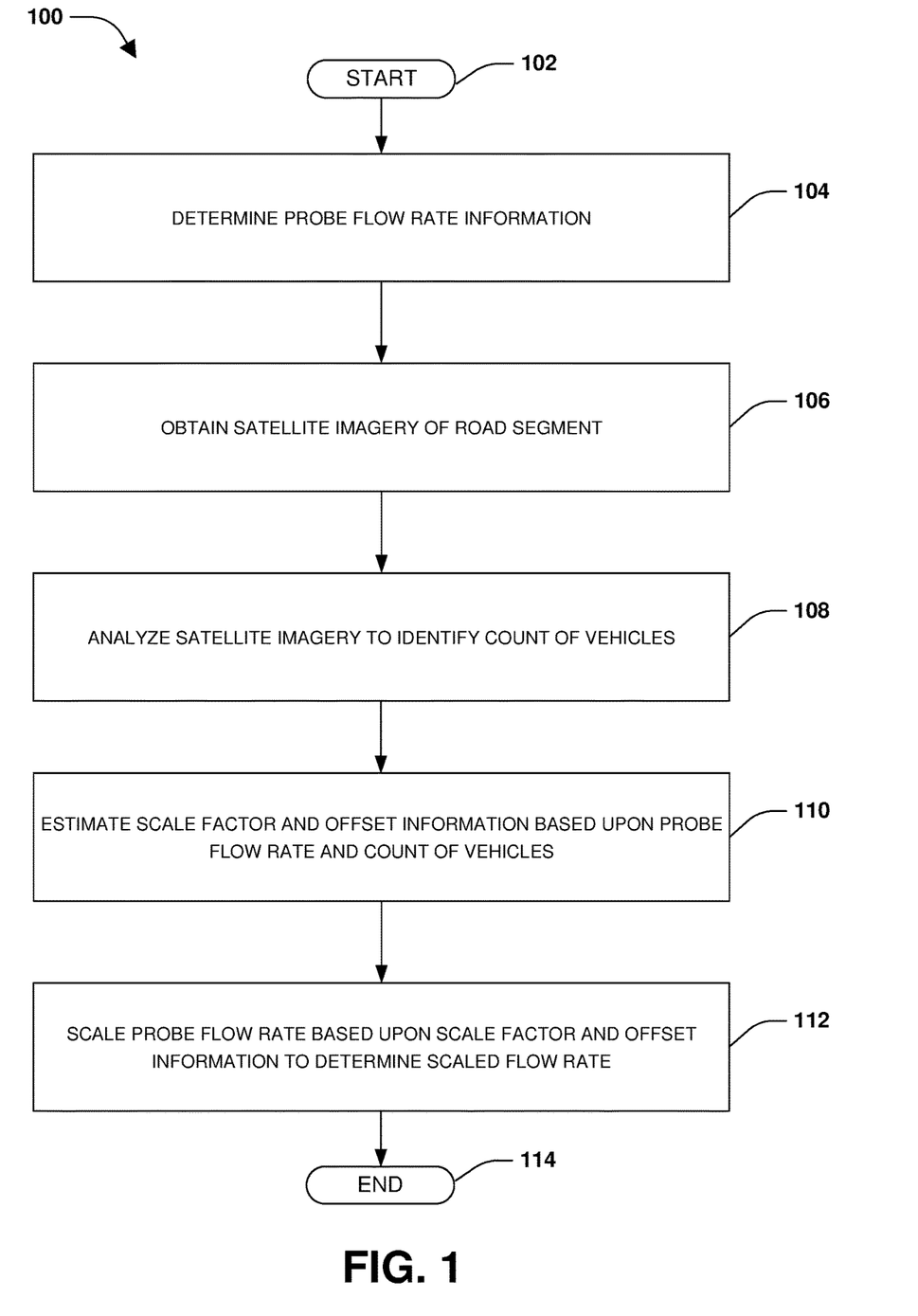
FIG. 1 is a flow diagram illustrating an exemplary method of determining a scaled flow rate of traffic for a road segment.

An embodiment of determining a scaled flow rate of traffic for a road segment is illustrated by an exemplary method 100 of FIG. 1. At 102, the method 100 starts. At 104, probe flow rate information may be determined based upon locational information from one or more probe vehicles on a road segment (e.g., a count of probe vehicles on the road segment). For example, the probe flow rate information may be derived from global positing system (GPS) coordinates and timestamp information provided by vehicle head units (e.g., a navigation device requesting a driving route), a mobile device (e.g., a map application hosted by a smartphone of a driver), a vehicle computing device, and/or other devices located within a vehicle. In an example, 3 probe vehicles may provide GPS coordinates and timestamp information while traveling the road segment.

At 106, satellite imagery (e.g., an image, video, etc.) of the road segment may be obtained. At 108, the satellite imagery may be analyzed to identify a count of vehicles on the road segment for a unit of time. In an example, the road segment may be identified within the satellite imagery based upon a linear feature indicative of the road segment. In another example, the road segment may be identified within the satellite imagery by overlaying a road network from a map onto the satellite imagery. In an example, a vehicle may be identified based upon an identification of a parallelogram or other shape within the satellite imagery. In another example, an image analysis algorithm may be utilized to identify the count of vehicles. The image analysis algorithm, such as an edge detection function or a threshold used by the image analysis algorithm, may be adjusted based upon the probe flow rate information and/or the locational information (e.g., locations of the 3 probe vehicles may be known, and thus the 3 probe vehicles may be identified within the satellite imagery based upon the locational information, which may be used as feedback to adjust the image analysis algorithm to detect other vehicles). In an example, 100 vehicles, including the 3 probe vehicles, may be identified as traveling along the road segment.

At 110, scale factor and offset information may be estimated based upon the probe flow rate information and the count of vehicles for the unit of time. For example, the scale factor and offset information may be derived from the knowledge that the 3 probe vehicles represented 3% of the 100 vehicles on the road segment. In an example, the scale factor and offset information may be estimated based upon the probe flow rate information and a ground flow rate determined by the count of vehicles. In an example, the scale factor and offset information may be averaged based upon a road type of the road segment, a day of the week, a number of lanes of the road segment, a season (e.g., winter driving conditions), road construction, a weather condition, and/or a variety of other factors.

At 112, the probe flow rate information may be scaled based upon the scale factor and offset information to determine a scaled flow rate. For example, a probe flow rate, as determined by the GPS coordinates and timestamps from the 3 probe vehicles, may be scaled to the 100 total vehicles to determine the scaled flow rate. The scaled flow rate may correspond to inferred traffic volume along the road segment. In an example, the scaled flow rate may be determined for a second unit of time, different than the unit of the time of the satellite imagery, in real-time based upon the probe flow rate information corresponding to real-time locational information of the one or more probe vehicles (e.g., the scale factor and offset information may be used to determine scaled flow rates for subsequent times, days, weeks, etc. such as in real-time). For example, real-time locational information (e.g., GPS coordinates and/or timestamps used to identify probe flow information) may be obtained from a set of probe vehicles traveling along the road segment (e.g., real-time locational information obtained a week after the scale factor and offset information was determined). The scale factor and offset information may be applied to the real-time locational information to determine a real-time flow rate for the road segment. In an example, the scale factor and offset information may be used with vehicle speed information and the probe flow rate information (e.g., a volume of probe vehicles on the road segment), to determine a traffic density. At 114, the method 100 ends.

Figure 2A:
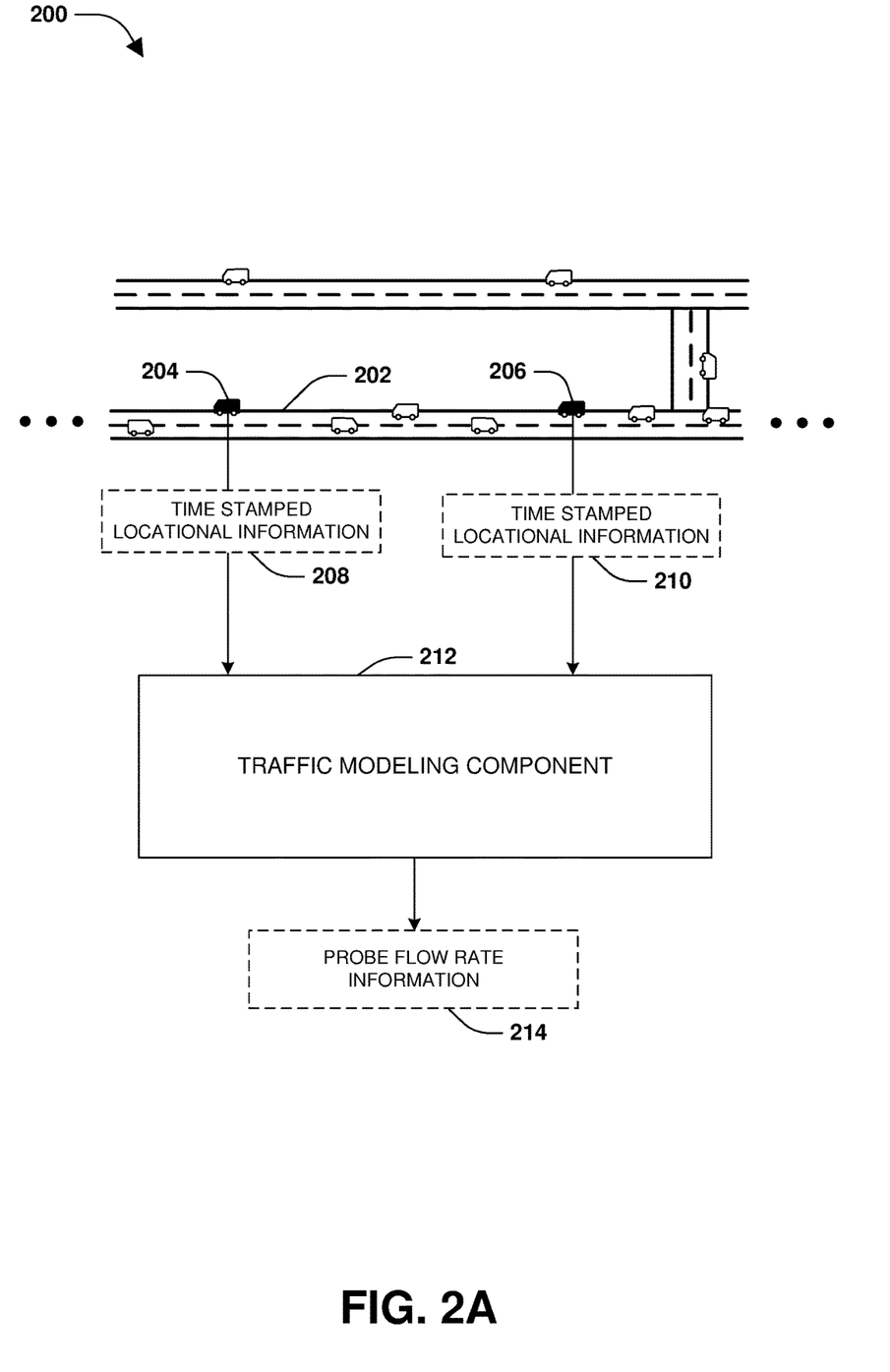
FIG. 2A is a component block diagram illustrating an exemplary system for determining a scaled flow rate of traffic for a road segment, where probe flow rate information is obtained.
Figure 2B:
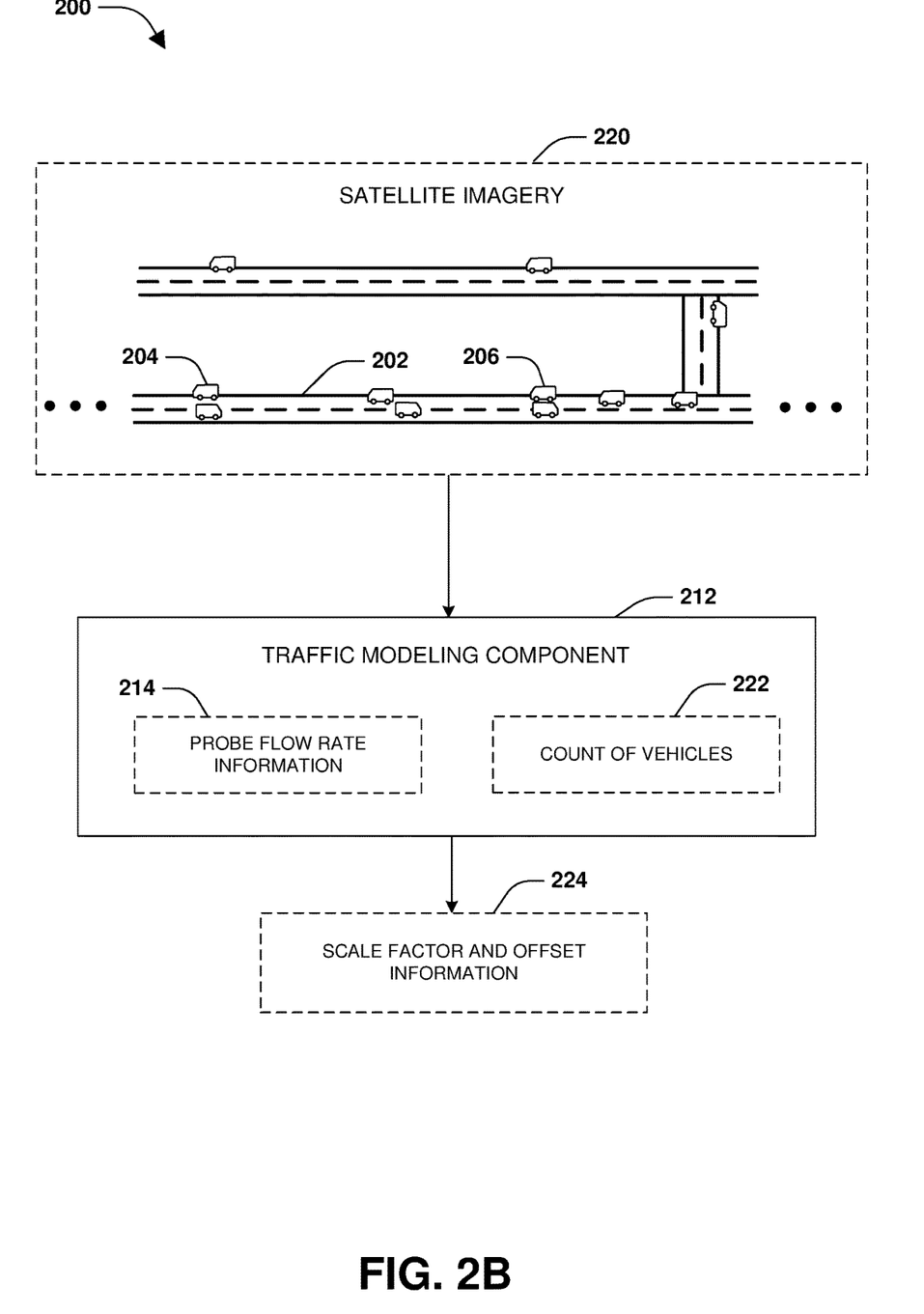
FIG. 2B is a component block diagram illustrating an exemplary system for determining a scaled flow rate of traffic for a road segment, where scale factor and offset information is estimated.
Figure 2C:
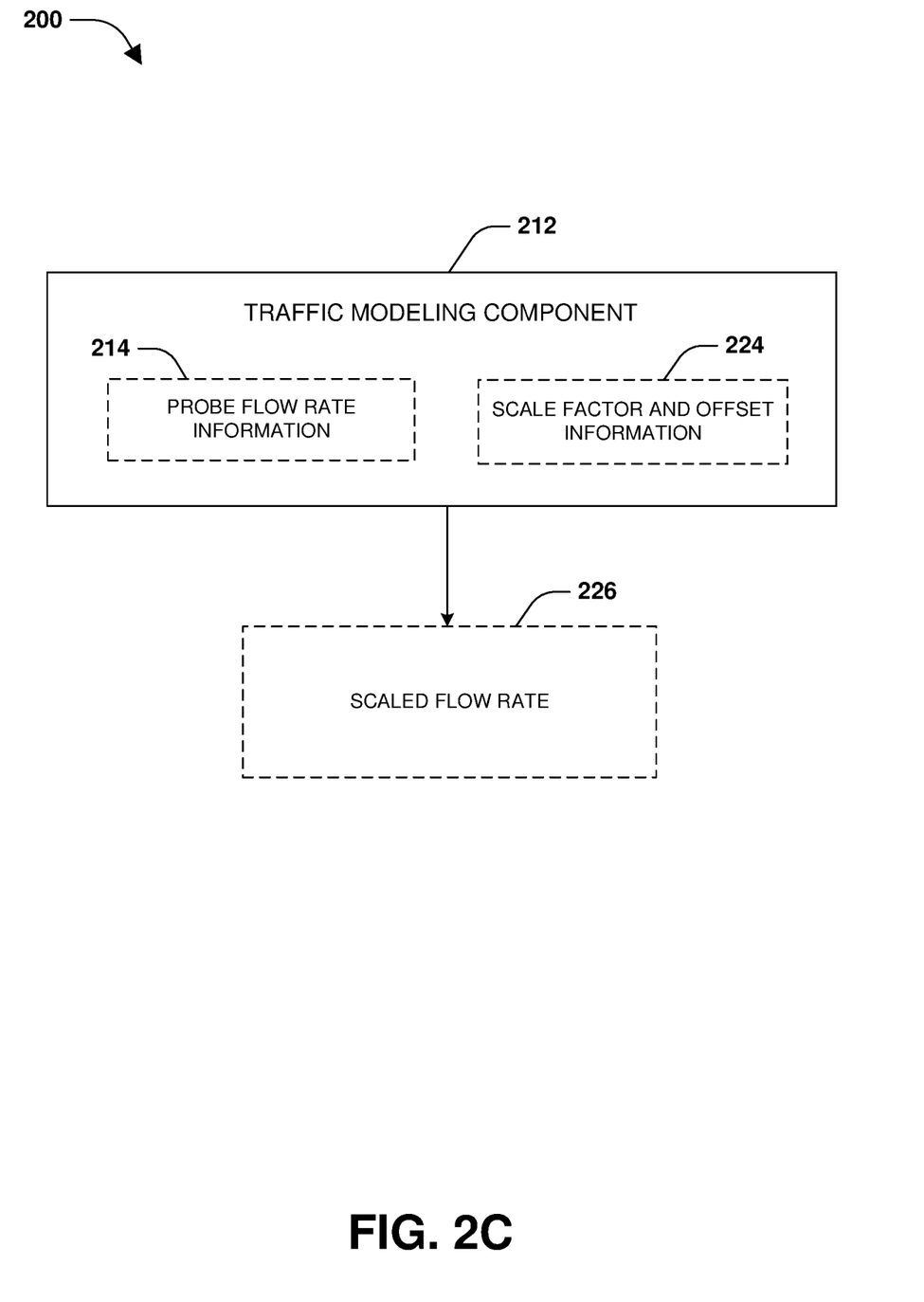
FIG. 2C is a component block diagram illustrating an exemplary system for determining a scaled flow rate of traffic for a road segment, where probe flow rate information is scaled based upon scale factor and offset information to determine a scaled flow rate.

FIGS. 2A-2C illustrate examples of a system 200, comprising a traffic modeling component 212, for determining a scaled flow rate of traffic for a road segment 202. The traffic modeling component 212 may establish communication connections with one or more probe vehicles, such as a first probe vehicle 204 and a second probe vehicle 206, traveling along the road segment 202. The traffic modeling component 212 may receive first time stamped locational information 208 (e.g., GPS coordinates) from the first probe vehicle 204, as illustrated in FIG. 2A. The traffic modeling component 212 may receive second time stamped locational information 210 from the second probe vehicle 206.

Probe flow traffic rate information 214 may be derived from the first time stamped locational information 208 and the second time stamped locational information 210. Because the probe flow rate information 214 may merely represent a fraction of the vehicles on the road segment 202, the probe flow rate information 214 will be scaled by a scale factor corresponding to the fraction of the traffic that the first probe vehicle 204 and the second probe vehicle 206 represent (e.g., the 2 probe vehicles and 78 non-probe vehicles may be traveling the road segment 202). Accordingly, as provided herein, a count of vehicles on the road segment 202 may be identified from satellite imagery in order to estimate relatively accurate scale factor and offset information to the apply to the probe flow rate information 214 (e.g., as opposed to merely estimating/guessing a number of vehicles on the road segment 202).

FIG. 2B illustrates an example of the traffic modeling component 212 obtaining satellite imagery 220. The traffic modeling component 212 may analyze the satellite imagery 220, such as using an image analysis algorithm, linear feature extraction, and/or overlaying a road network of a map onto the satellite imagery 220, to identify the road segment 202. The traffic modeling component 212 may analyze the satellite imagery 220, such as using the image analysis algorithm and/or shape feature extraction (e.g., identification of parallelograms indicative of vehicles), to identify a count of vehicles 222 on the road segment 202 (e.g., 80 vehicles corresponding to the 2 probe vehicles and the 78 non-probe vehicles). The traffic modeling component 212 may estimate scale factor and offset information 224 based upon the probe flow rate information 214 and the count of vehicles 222 on the road segment 202. The scale factor and offset information 224 may comprising scaling and/or offset values used to scale the probe flow rate information 214 (e.g., a probe flow rate) from the 2 probe vehicles to a scale flow rate for the 80 total vehicles. FIG. 2C illustrates the traffic modeling component 212 scaling the probe flow rate information 214 based upon the scale factor and offset information 224 to determine a scaled flow rate 226 for the road segment 202 (e.g., flow rate of the 2 probe vehicles may be scaled to a flow rate of the 80 total vehicles on the road segment 202).

Figure 3:
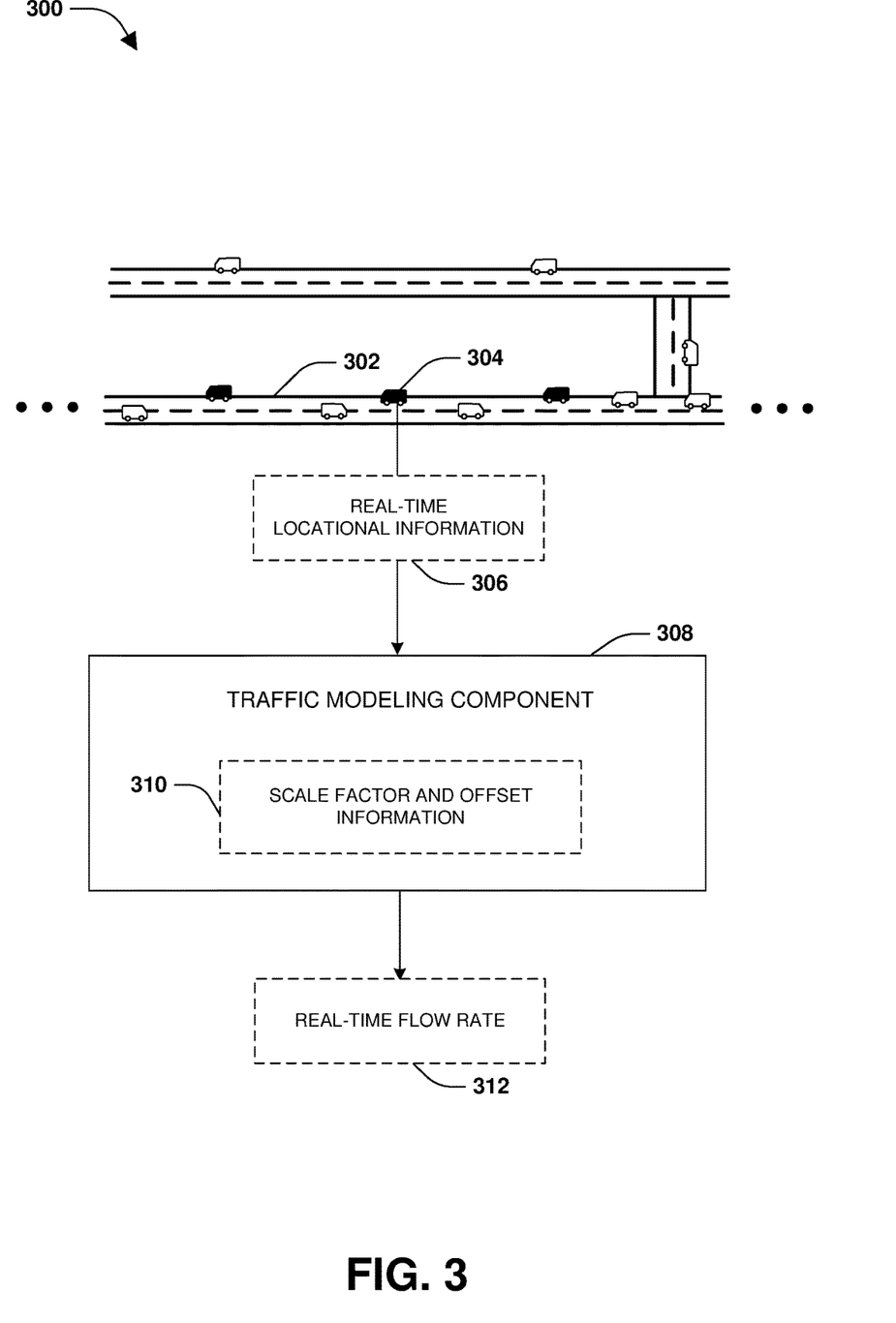
FIG. 3 is a component block diagram illustrating an exemplary system for determining a real-time flow rate of traffic for a road segment.

FIG. 3 illustrates an example of a system 300, comprising a traffic modeling component 308, for determining a real-time flow rate 312 (e.g., a scaled flow rate) of a road segment 302 (e.g., a road segment corresponding to road segment 202 of FIGS. 2A-2C). The traffic modeling component 308 may obtain real-time locational information 306 from a set of probe vehicles, such as a probe vehicle 304, traveling along the road segment 302. The traffic modeling component 308 may maintain scale factor and offset information 310 for the road segment 302 (e.g., scale factor and offset information 224 of FIG. 2B). The traffic modeling component 308 may apply the scale factor and offset information 310 to the real-time locational information 306 to determine a real-time flow rate 312 for the road segment 302. In this way, real-time flow rates may be estimated for the road segment 302 by applying the scale factor and offset information 310 to real-time locational information.

Figure 4:
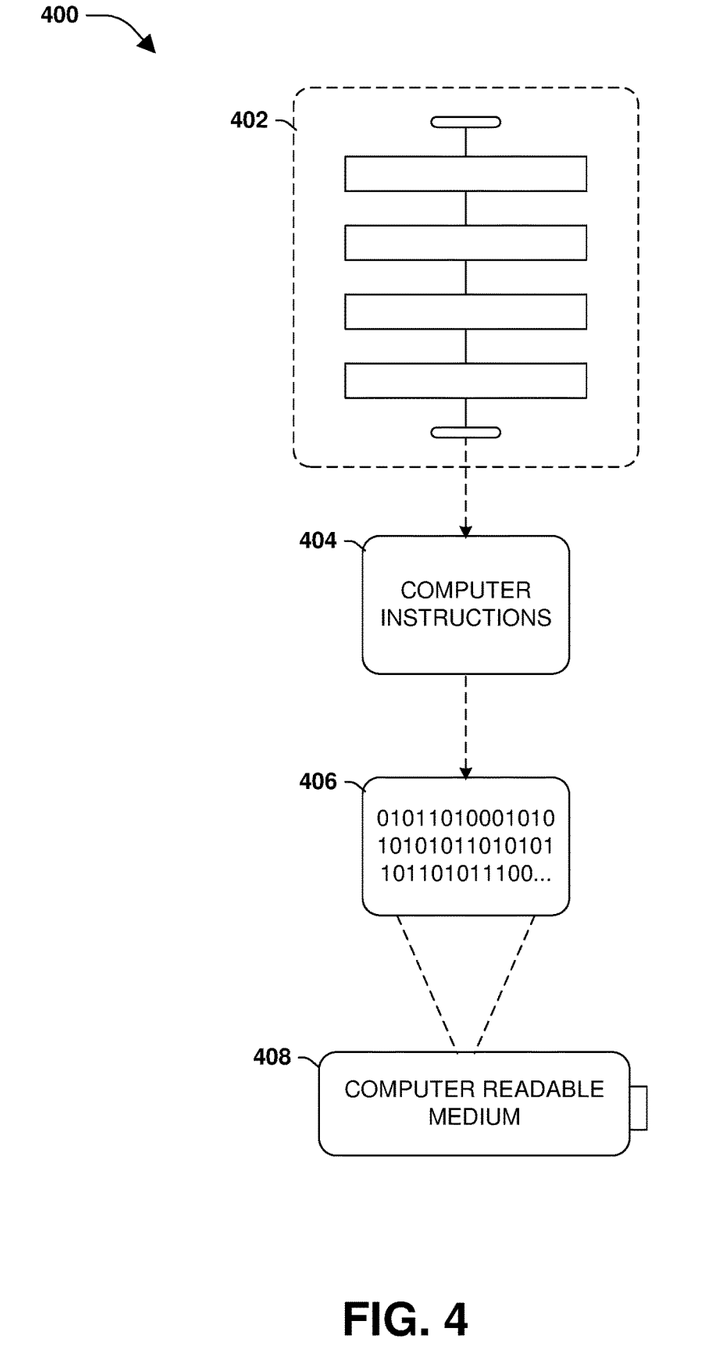
FIG. 4 is an illustration of an exemplary computer readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device is illustrated in FIG. 4, wherein the implementation 400 comprises a computer-readable medium 408, such as a CD-R, DVD-R, flash drive, a platter of a hard disk drive, etc., on which is encoded computer-readable data 406. This computer-readable data 406, such as binary data comprising at least one of a zero or a one, in turn comprises a set of computer instructions 404 configured to operate according to one or more of the principles set forth herein. In some embodiments, the set of computer instructions 404 are configured to perform a method 402, such as at least some of the exemplary method 100 of FIG. 1, for example. In some embodiments, the set of computer instructions 404 are configured to implement a system, such as at least some of the exemplary system 200 of FIGS. 2A-2C and/or at least some of the exemplary system 300 of FIG. 3, for example. Many such computer-readable media are devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

As used in this application, the terms "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 5:
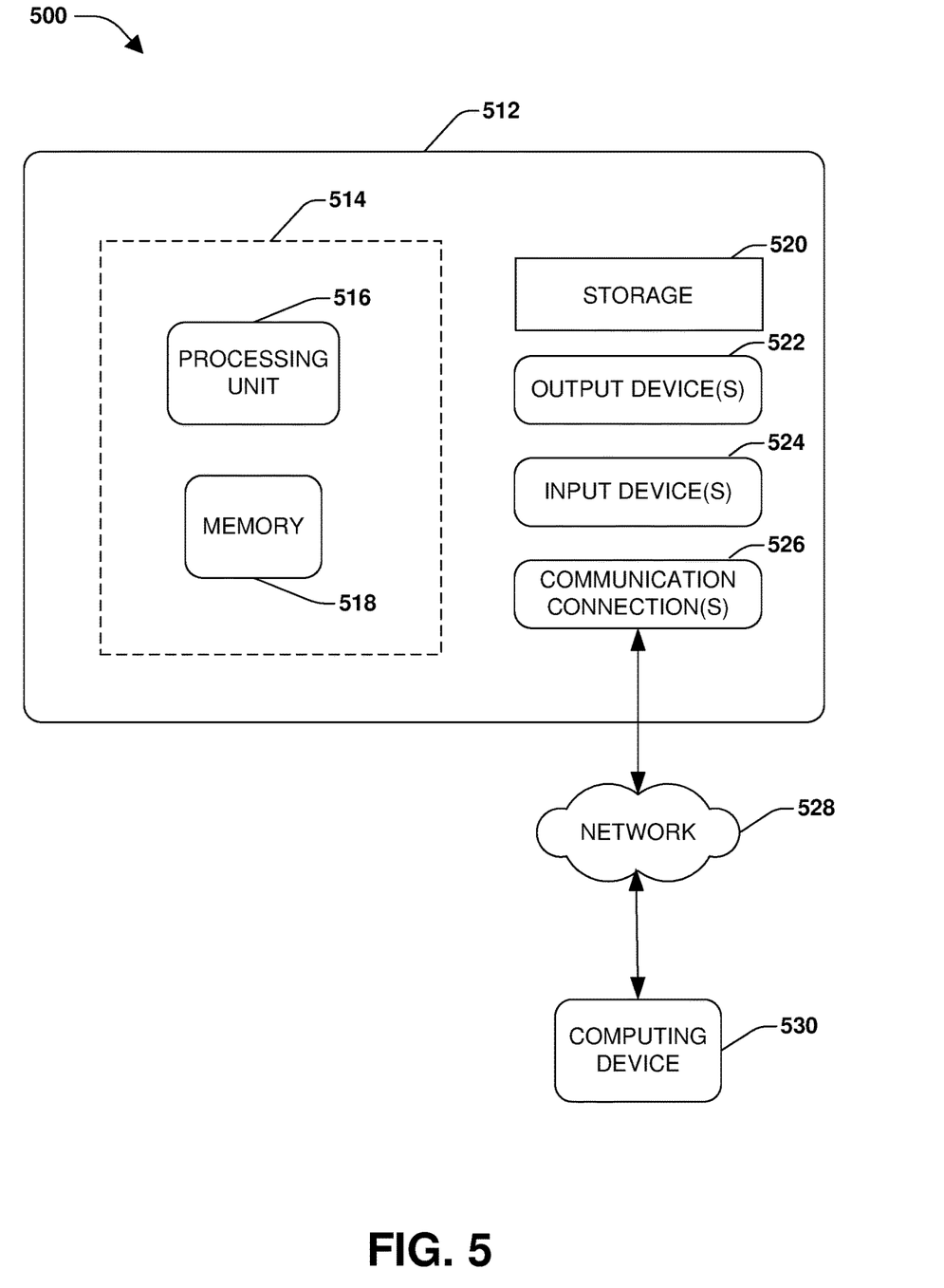
FIG. 5 illustrates an exemplary computing environment wherein one or more of the provisions set forth herein may be implemented.

FIG. 5 and the following discussion provide a brief, general description of a suitable computing environment to implement embodiments of one or more of the provisions set forth herein. The operating environment of FIG. 5 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 5 illustrates an example of a system 500 comprising a computing device 512 configured to implement one or more embodiments provided herein. In one configuration, computing device 512 includes at least one processing unit 516 and memory 518. Depending on the exact configuration and type of computing device, memory 518 may be volatile (such as RAM, for example), non-volatile (such as ROM, flash memory, etc., for example) or some combination of the two. This configuration is illustrated in FIG. 5 by dashed line 514.

In other embodiments, device 512 may include additional features and/or functionality. For example, device 512 may also include additional storage (e.g., removable and/or non-removable) including, but not limited to, magnetic storage, optical storage, and the like. Such additional storage is illustrated in FIG. 5 by storage 520. In one embodiment, computer readable instructions to implement one or more embodiments provided herein may be in storage 520. Storage 520 may also store other computer readable instructions to implement an operating system, an application program, and the like. Computer readable instructions may be loaded in memory 518 for execution by processing unit 516, for example.

The term "computer readable media" as used herein includes computer storage media. Computer storage media includes volatile and nonvolatile, removable and non-removable media implemented in any method or technology for storage of information such as computer readable instructions or other data. Memory 518 and storage 520 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 512. Computer storage media does not, however, include propagated signals. Rather, computer storage media excludes propagated signals. Any such computer storage media may be part of device 512.

Device 512 may also include communication connection(s) 526 that allows device 512 to communicate with other devices. Communication connection(s) 526 may include, but is not limited to, a modem, a Network Interface Card (NIC), an integrated network interface, a radio frequency transmitter/receiver, an infrared port, a USB connection, or other interfaces for connecting computing device 512 to other computing devices. Communication connection(s) 526 may include a wired connection or a wireless connection. Communication connection(s) 526 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 512 may include input device(s) 524 such as keyboard, mouse, pen, voice input device, touch input device, infrared cameras, video input devices, and/or any other input device. Output device(s) 522 such as one or more displays, speakers, printers, and/or any other output device may also be included in device 512. Input device(s) 524 and output device(s) 522 may be connected to device 512 via a wired connection, wireless connection, or any combination thereof. In one embodiment, an input device or an output device from another computing device may be used as input device(s) 524 or output device(s) 522 for computing device 512.

Components of computing device 512 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 512 may be interconnected by a network. For example, memory 518 may be comprised of multiple physical memory units located in different physical locations interconnected by a network.

Those skilled in the art will realize that storage devices utilized to store computer readable instructions may be distributed across a network. For example, a computing device 530 accessible via a network 528 may store computer readable instructions to implement one or more embodiments provided herein. Computing device 512 may access computing device 530 and download a part or all of the computer readable instructions for execution. Alternatively, computing device 512 may download pieces of the computer readable instructions, as needed, or some instructions may be executed at computing device 512 and some at computing device 530.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "exemplary" is used herein to mean serving as an example, instance, illustration, etc., and not necessarily as advantageous. As used herein, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B and/or both A and B. Furthermore, to the extent that "includes", "having", "has", "with", and/or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A system for determining a scaled flow rate of traffic for a road segment, comprising:
a traffic modeling component, implemented via a processor, configured to:
determine probe flow rate information based upon locational information from one or more probe vehicles on a road segment;
obtain satellite imagery of the road segment;
analyze the satellite imagery to identify a count of vehicles on the road segment for a unit of time;
estimate scale factor and offset information based upon the probe flow rate information and the count of vehicles for the unit of time; and
scale the probe flow rate information based upon the scale factor and offset information to determine a scaled flow rate.

2. The system of claim 1, the traffic modeling component configured to:
identify a linear feature for identifying the road segment within the satellite imagery.

3. The system of claim 1, the traffic modeling component configured to:
overlay a road network onto the satellite imagery for identifying the road segment within the satellite imagery.

4. The system of claim 1, the traffic modeling component configured to:
identify a parallelogram for identifying a vehicle within the satellite imagery.

5. The system of claim 1, the traffic modeling component configured to:
determine a ground flow rate based upon the count of vehicles; and
estimate the scale factor and offset information based upon the probe flow rate information and the ground flow rate.

6. The system of claim 1, the traffic modeling component configured to:
determine the scaled flow rate for a second unit of time, different than the unit of time, in real-time based upon the probe flow rate information corresponding to real-time locational information of the one or more probe vehicles.

7. The system of claim 1, the traffic modeling component configured to:
obtain real-time locational information from a set of probe vehicles traveling along the road segment; and
apply the scale factor and offset information to the real-time locational information to determine a real-time flow rate for the road segment.

8. The system of claim 1, the locational information corresponding to a timestamp and global positioning system (GPS) coordinates of at least one of a vehicle head unit, a vehicle computing device, or a mobile device located within a vehicle.

9. The system of claim 1, the traffic modeling component configured to:
average the scale factor and offset information based upon at least one of a road type, a day of week, a number of lanes per road, a season, road construction, or a weather condition.

10. The system of claim 1, the traffic modeling component configured to:
utilize vehicle speed information, the probe flow rate information, and the scale factor and offset information to determine a traffic density.

11. The system of claim 1, the scaled flow rate corresponding to inferred traffic volume along the road segment.

12. The system of claim 1, the traffic modeling component configured to:
utilize an image analysis algorithm to identify the count of vehicles from the satellite imagery.

13. The system of claim 12, the traffic modeling component configured to:
utilize the locational information to identify one or more identified probe vehicles on the road segment; and
adjust the image analysis algorithm based upon the one or more identified probe vehicles.

14. The system of claim 13, the traffic modeling component configured to:
adjust at least one of an edge detection function or a threshold used by the image analysis algorithm based upon the one or more identified probe vehicles.

15. A method for determining a scaled flow rate of traffic for a road segment, comprising:
determining probe flow rate information based upon locational information from one or more probe vehicles on a road segment;
obtaining satellite imagery of the road segment;
analyzing the satellite imagery to identify a count of vehicles on the road segment for a unit of time;
estimating scale factor and offset information based upon the probe flow rate information and the count of vehicles for the unit of time; and
scaling the probe flow rate information based upon the scale factor and offset information to determine a scaled flow rate.

16. The method of claim 15, comprising:
obtaining real-time locational information from a set of probe vehicles traveling along the road segment; and
applying the scale factor and offset information to the real-time locational information to determine a real-time flow rate for the road segment.

17. The method of claim 15, comprising:
utilizing an image analysis algorithm to identify the count of vehicles from the satellite imagery;
utilizing the locational information to identify one or more identified probe vehicles on the road segment; and
adjusting the image analysis algorithm based upon the one or more identified probe vehicles.

18. The method of claim 15, comprising:
averaging the scale factor and offset information based upon at least one of a road type, a day of week, a number of lanes per road, a season, road construction, or a weather condition.

19. The method of claim 15, the estimating comprising:
determining a ground flow rate based upon the count of vehicles; and
estimating the scale factor and offset information based upon the probe flow rate information and the ground flow rate.

20. A non-transitory computer readable medium comprising instructions which when executed perform a method for determining a scaled flow rate of traffic for a road segment, comprising:
determining probe flow rate information based upon locational information from one or more probe vehicles on a road segment;
obtaining satellite imagery of the road segment;
analyzing the satellite imagery to identify a count of vehicles on the road segment for a unit of time;

estimating scale factor and offset information based upon the probe flow rate information and the count of vehicles for the unit of time; and scaling the probe flow rate information based upon the scale factor and offset information to determine a scaled flow rate.

* * * * *